(12) United States Patent
Laiso

(10) Patent No.: US 12,364,726 B2
(45) Date of Patent: Jul. 22, 2025

(54) COMPOSITION FOR OBTAINING A NATURAL BIOACTIVE FOR ONCOLOGIC THERAPIES

(71) Applicant: Angelica Machado Mey, Campinas (BR)

(72) Inventor: Rosa Andrea Nogueira Laiso, São Paulo (BR)

(73) Assignee: Angelica Machado Mey, Campinas-SP (BR)

( * ) Notice: Subject to any disclaimer, the term of this patent is extended or adjusted under 35 U.S.C. 154(b) by 436 days.

(21) Appl. No.: 18/079,931

(22) Filed: Dec. 13, 2022

(65) Prior Publication Data

US 2023/0285486 A1    Sep. 14, 2023

(30) Foreign Application Priority Data

Mar. 8, 2022    (BR) .......................... 102022004270-5
Oct. 31, 2022   (BR) .......................... 102022022061-1

(51) Int. Cl.

| | | |
|---|---|---|
| *A61K 36/19* | (2006.01) | |
| *A61K 35/00* | (2006.01) | |
| *A61K 47/02* | (2006.01) | |
| *A61K 47/24* | (2006.01) | |
| *A61P 35/00* | (2006.01) | |

(52) U.S. Cl.
CPC ............. *A61K 36/19* (2013.01); *A61K 47/02* (2013.01); *A61K 47/24* (2013.01); *A61P 35/00* (2018.01)

(58) Field of Classification Search
CPC ......... A61K 36/19; A61K 47/02; A61K 31/13
See application file for complete search history.

(56) References Cited

U.S. PATENT DOCUMENTS

2006/0264510 A1* 11/2006 Halstead ................ A61K 36/30
514/566

* cited by examiner

*Primary Examiner* — Kyle A Purdy
(74) *Attorney, Agent, or Firm* — B. Aaron Schulman, Esq.; Stites & Harbison, PLLC

(57) ABSTRACT

The present invention refers to a composition for obtaining a natural bioactive for oncologic therapies based on *Andrographis paniculata*, whose excipient is phosphoryl ethanol amine, and optionally carbonates. The function of the composition is to assist treatments of several types of cancer, and it may be administered as an auxiliary adjuvant in oncologic therapies. Since it consists of diterpenoids, flavonoids and polyphenols as the main bioactive components, it has an anti-inflammatory, antiviral, antibacterial, antioxidant, antiparasitic, antispasmodic, antidiabetic, antipyretic, nematocidal, immunomodulatory and immunostimulatory action. The composition for obtaining a natural bioactive for oncologic therapies comprises: Active principle: *Andrographis paniculata*, and Excipient: phosphoryl ethanol amine. Optionally, the excipients are comprised of: Phosphoryl ethanol amine-Calcium Carbonate; and Magnesium Carbonate.

2 Claims, No Drawings

COMPOSITION FOR OBTAINING A NATURAL BIOACTIVE FOR ONCOLOGIC THERAPIES

The present invention refers to a composition for obtaining a natural bioactive for oncologic therapies based on *Andrographis paniculata* (Brum. F.) Nees (Acanthaceae), a plant widely used in Chinese traditional medicine (CTM), native of Taiwan, Continental China and India (Huang & Wu, 2002), whose excipient is phosphoryl ethanol amine, and optionally carbonates. The function of the composition is to assist treatments of several types of cancer, and it may be administered as an auxiliary adjuvant in oncologic therapies. Since it consists of diterpenoids, flavonoids and polyphenols as the main bioactive components, it has an anti-inflammatory, antiviral, antibacterial, antioxidant, antiparasitic, antispasmodic, antidiabetic, antipyretic, nematocidal, immunomodulatory and immunostimulatory action (Rao et al., 2004; Niranjan et al., (2010), through which practical, safe and functional results were obtained.

BACKGROUND OF THE INVENTION

The *A. paniculata* extract has been widely used in medicinal and pharmacological applications, in different traditional medicine systems, has anti-inflammatory, antiviral, antibacterial, antioxidant, antiparasitic, antispasmodic, antidiabetic, antipyretic, nematocidal, antitumor activities and inhibits significantly the proliferation of HT-29 cells (colon cancer), MDA MB-231 (human triple negative breast cancer), and B16-F10 (melanoma), is an immunomodulator and immunostimulant, and increases the proliferation of peripheral blood lymphocytes in humans.

Another important administration activity of *A. paniculata* is the hepatoprotective action thereof, and it was noticed that the administration of the extract provided a dose-dependent significant protection against induced hepatotoxicity, evaluated in terms of biochemical and histopathological parameters. Thus regulating glutamate pyruvate transaminase (GPT), serum glutamate oxaloacetate transaminase (GOT) alkaline phosphatase (ALP) and bilirubin in the peripheral blood serum, and distorted architecture of hepatic tissue, together with increased levels of peroxide lipids (LPO) and reduced superoxide dismutase (SOD), catalase, reduced glutathione (GSH) and glutathione peroxidase (GPx) in the hepatic tissue after being administered (Nagalekshmi et al., 2011).

It is a potent remover of oxygen reactive species (ORS) including anion superoxide, hydroxyl radical, singlet oxygen, peroxy nitrite, and nitric acid. Among several active chemical constituents are andrographolide, neoandrographolide and dehydroandrographolide which are the most important bioprotectors for a wide range of therapeutic applications. Andrographolide significantly inhibits the expression of iNOS, COX-2, mRNA, proteins and enzyme activity in RAW 264.7 macrofages which involve an anti-inflammatory activity. The extract of *Andrographis paniculata* protects lipids, hemoglobin and red cells against lipid peroxidation. It prevents oxidative damages and prevents toxic metabolites from linking to the DNA.

Phosphoryl ethanol amide is an excipient already known in the market as a carrier of several drugs, and in view of its molecular characteristic exhibits a high bioavailability and improvement in the pharmacokinetics thereof and when associated to other drugs. It is available in the market with excipient phosphoryl ethanol amine, including chemotherapeutics such as Caelyx® and Doxopeg®, and medications for obesity such as IMCIVREE™ (setmelanotide).

STATE OF THE ART

Both in national and international markets, it is possible to find phytotherapeutical *A. paniculata* for treating several diseases, and phosphoryl ethanol amine as an excellent excipient and carrier, potentializing the action of other inputs in view of its ability to improve both biodistribution and pharmacokinetics. The main drawback is the toxicity of *A. paniculata* at high concentrations and/or the long-term administration, which characteristic is not present in concentrations associated with excipient phosphoryl ethanol amine, thus exhibiting a protective effect for a large number of normal cells, and generating an important additive effect with high toxicity in tumor cells which are able to resist to multiple drugs such as triple negative breast cancer (MDA-MB 231).

OBJECT OF THE INVENTION

Thus, the object of the invention is to provide a new composition combining an active principle and at least an excipient which is more effective when present at concentrations of 10 to 30% *A. paniculata* associated to phosphoryl ethanol amine at concentrations of 70 to 90% in tumor cells with a resistance profile without causing any harm to normal cells. As the concentration of *A. paniculata* increases in relation to phosphoryl ethanol amine, the antiviral, antibacterial, antioxidant, antiparasitic, antispasmodic, nematocidal, immunostimulant and antioxidant activities are highlighted. Optionally, other excipients such as carbonates will be added.

SUMMARY OF THE INVENTION

The composition for providing a natural bioactive for oncological therapies comprises:
Active principle: *Andrographis paniculata*; and
Excipient: phosphoryl ethanol amine
Optionally, the excipients will comprise:
phosphoryl ethanol amine;
calcium carbonate; and
magnesium carbonate.

DETAILED DESCRIPTION OF THE INVENTION

The composition for providing a natural bioactive for oncologic therapies comprises the following compounds, by weight:
Active principle: 10 to 30% *Andrographis paniculata*, with at least 10% and rog rapholides;
Excipient: 70 to 90% phosphoryl ethanol amine.
Optionally, the excipients will comprise:
50 to 60% phosphoryl ethanol amine;
17.5 to 25% calcium carbonate; and
2.5 to 5% magnesium carbonate.

Examples of Accomplishments

As examples of how to obtain the composition, experiments were conducted where the concentration of products is described in millimolar (mM) in a 24-hour period for analyses and comparisons.

The object is to provide a IC 50% with the respective associations, meaning a required amount or concentration of product to kill 50% of a cell culture which is comprised of normal cells (human fibroblast FN1 was used with healthy cells) or a culture of tumor cells (triple negative breast cancer was used).

An ideal innovative compound would be one having a minimum concentration, IC 50% of a culture of ill cells and a much higher proportion to reach IC 50% of normal cells. This means that all sick cells would die before any normal cell was attacked, that is, an effective compound without side effects wherein the higher the content the better the compound, where we have:

Index=IC 50% tumor cell (mM)÷IC 50% normal cell (mM)

In experiments 1 to 4 only one active principle (*Andrographis paniculata*) and one excipient (phosphoryl ethanol amine) were used.

EXPERIMENT 1: In this experiment, the following concentrations were used, totaling 100% equivalent to 100 mg:
Active principle: 99.5% *Andrographis paniculata* equivalent to 99.5 mg; and
Excipient: 0.5% phosphoryl ethanol amine equivalent to 5 mg.

Table 1 shows the results of the respective experiment:

| IC 50% Tumor cells (mM) | IC 50% Normal cells (mM) | Index | Efficacy (Tumor cell) | Regular Noxiousness |
|---|---|---|---|---|
| 4.57 | 8.76 | 1.9 | HIGH | MEDIUM |

EXPERIMENT 2: In this experiment, the following concentrations were used, totaling 100% equivalent to 100 mg:
Active principle: 50% *Andrographis paniculata* equivalent to 50 mg; and
Excipient: 50% phosphoryl ethanol amine equivalent to 50 mg.

Table 2 shows the results of the respective experiment:

| IC 50% Tumor cells (mM) | IC 50% Normal cells (mM) | Index | Efficacy (Tumor cell) | Regular Noxiousness |
|---|---|---|---|---|
| 17.4 | 26.25 | 1.9 | LOW | LOW |

EXPERIMENT 3: In this experiment, the following concentrations were used, totaling 100% equivalent to 100 mg:
Active principle: 30% *Andrographis paniculata* equivalent to 30 mg; and
Excipient: 70% phosphoryl ethanol amine equivalent to 70 mg.

Table 3 shows the results of the respective experiment:

| IC 50% Tumor cells (mM) | IC 50% Normal cells (mM) | Index | Efficacy (Tumor cell) | Regular Noxiousness |
|---|---|---|---|---|
| 18.26 | 21.97 | 1.4 | LOW | LOW |

EXPERIMENT 4: In this experiment, the following concentrations were used, totaling 100% equivalent to 100 mg:
Active principle: 10% *Andrographis paniculata* equivalent to 10 mg; and
Excipient: 90% phosphoryl ethanol amine equivalent to 90 mg.

Table 4 shows the results of the respective experiment:

| IC 50% Tumor cells (mM) | IC 50% Normal cells (mM) | Index | Efficacy (Tumor cell) | Regular Noxiousness |
|---|---|---|---|---|
| 18.26 | 21.97 | 1.4 | LOW | LOW |

In experiments 5 to 8, one active principle (*Andrographis paniculata*) and three excipients: (phosphoryl ethanol amine+calcium carbonate+magnesium carbonate) were used.

EXPERIMENT 5: In this experiment, the following concentrations were used, totaling 100% equivalent to 100 mg:
Active principle: 99.5% *Andrographis paniculata* equivalent to 99.5 mg; and
Excipient: 0.5% phosphoryl ethanol amine equivalent to 5 mg.

Table 5 shows the results of the respective experiment:

| IC 50% Tumor cells (mM) | IC 50% Normal cells (mM) | Index | Efficacy (Tumor cell) | Regular Noxiousness |
|---|---|---|---|---|
| 4.57 | 8.76 | 1.9 | HIGH | MEDIUM |

EXPERIMENT 6: In this experiment, the following concentrations were used, totaling 100% equivalent to 100 mg:
Active principle: 50% *Andrographis paniculata* equivalent to 50 mg; and
Excipient: 50% phosphoryl ethanol amine equivalent to 50 mg.

Table 6 shows the results of the respective experiment:

| IC 50% Tumor cells (mM) | IC 50% Normal cells (mM) | Index | Efficacy (Tumor cell) | Regular Noxiousness |
|---|---|---|---|---|
| 3.54 | 20.31 | 5.7 | HIGH | LOW |

EXPERIMENT 7: In this experiment, the following concentrations were used, totaling 100% equivalent to 100 mg:
Active principle: 30% *Andrographis paniculata* equivalent to 30 mg; and
Excipient: 70% phosphoryl ethanol amine equivalent to 70 mg.

Table 7 shows the results of the respective experiment:

| IC 50% Tumor cells (mM) | IC 50% Normal cells (mM) | Index | Efficacy (Tumor cell) | Regular Noxiousness |
|---|---|---|---|---|
| 3.21 | 22.34 | 7.0 | HIGH | LOW |

EXPERIMENT 8: In this experiment, the following concentrations were used, totaling 100% equivalent to 100 mg:
Active principle: 10% *Andrographis paniculata* equivalent to 10 mg; and
Excipient: 90% phosphoryl ethanol amine equivalent to 90 mg.

Table 8 shows the results of the respective experiment:

| IC 50% Tumor cells (mM) | IC 50% Normal cells (mM) | Index | Efficacy (Tumor cell) | Regular Noxiousness |
|---|---|---|---|---|
| 2.47 | 26.47 | 10.7 | VERY HIGH | LOW |

After analyzing the experiments, the excellency of the result was attained by associating 10% of active principle *Andrographis paniculata* and 90% of excipient phosphoryl ethanol amine.

Advantages of the Invention

With the composition obtained as shown herein, besides enhancing the effects in tumor cells, it will surely provide several benefits such as:
- immunomodulator and immunostimulant;
- hepato-protector;
- antitumoral;
- anti-angiogenic;
- pro-apoptotic;
- better response to cells which are resistant to multiple drugs;
- anti-inflammatory activity;
- antioxidant action;
- antiviral;
- antibacterial;
- antiparasitic;
- antispasmodic.

Therefore, the scope of the present patent application shall not be limited to the example of obtaining same, but only to terms defined in the claims and equivalents thereof.

REFERENCES

Huang C J, Wu M C: Efeitos diferenciais de alimentos tradicionalmente considerados como 'aquecimento' e 'resfriamento' na produção de prostaglandina E 2 por uma linhagem celular de macrófagos. J Biomed Sci. 2002, 9: 596-606

Nagalekshmi, R., Menon, A., Chandrasekharan, D. K., & Nair, C. K. K. (2011). Hepatoprotective activity of *Andrographis paniculata* and *Swertia chirayita*. Food and Chemical Toxicology, 49(12), 3367-3373 Niranjan, A., Tewari, S. K., & Lehri, A. (2010). Biological activities of kalmegh (*Andrographis paniculata* Nees).

Rao Y K, Vimalamma G, Rao C V, Tzeng Y: Flavonoids and andrographolides from *Andrographis paniculata*. Phytochemistry. 2004, 65: 2317-2321. 10.1016/j.phytochem.2004.05.008.

The invention claimed is:

1. A composition for oncologic therapy, the composition comprising by weight: an active principle, wherein the active principle is 10% to 35% *Andrographis paniculata*; and three excipients, wherein the three excipients comprise 50% to 60% phosphoryl ethanol amine, 17.5 to 25% calcium carbonate, and 2.5 to 5% magnesium carbonate.

2. The composition according to claim 1, wherein the active principle *Andrographis paniculata* contains at least 20% andrographolides by weight.

* * * * *